(12) United States Patent
Kumagai et al.

(10) Patent No.: US 12,427,113 B2
(45) Date of Patent: Sep. 30, 2025

(54) CELLULOSE COMPOSITION, TABLET, AND ORALLY DISINTEGRATING TABLET

(71) Applicant: ASAHI KASEI KABUSHIKI KAISHA, Tokyo (JP)

(72) Inventors: Tadahiro Kumagai, Tokyo (JP); Yuji Hayashi, Tokyo (JP)

(73) Assignee: ASAHI KASEI KABUSHIKI KAISHA, Tokyo (JP)

(*) Notice: Subject to any disclaimer, the term of this patent is extended or adjusted under 35 U.S.C. 154(b) by 697 days.

(21) Appl. No.: 17/768,659

(22) PCT Filed: Nov. 7, 2019

(86) PCT No.: PCT/JP2019/043581
§ 371 (c)(1),
(2) Date: Apr. 13, 2022

(87) PCT Pub. No.: WO2021/090421
PCT Pub. Date: May 14, 2021

(65) Prior Publication Data
US 2023/0059899 A1 Feb. 23, 2023

(51) Int. Cl.
*A61K 9/20* (2006.01)
*A61K 9/00* (2006.01)

(52) U.S. Cl.
CPC .......... *A61K 9/2054* (2013.01); *A61K 9/0056* (2013.01); *A61K 9/2018* (2013.01)

(58) Field of Classification Search
None
See application file for complete search history.

(56) References Cited

U.S. PATENT DOCUMENTS

| 5,576,014 | A | * | 11/1996 | Mizumoto | ........... | A61K 9/2018 424/435 |
| 9,267,050 | B2 | | 2/2016 | Heiskanen et al. | | |
| 9,592,199 | B2 | * | 3/2017 | Obae | ......... | C08L 1/02 |

| 2015/0110900 | A1 | 4/2015 | Obae et al. |
| 2015/0150804 | A1 | 6/2015 | Obae et al. |
| 2015/0238424 | A1 | 8/2015 | Hiramura et al. |
| 2019/0008749 | A1 | 1/2019 | Harris et al. |

FOREIGN PATENT DOCUMENTS

| CN | 103893141 | | 7/2014 |
| EA | 013211 | B1 | 4/2010 |
| JP | 57-195101 | | 11/1982 |
| JP | 11-217401 | | 8/1999 |
| JP | 11-263723 | | 9/1999 |
| JP | 2000-016930 | | 1/2000 |
| JP | 2001-172430 | | 6/2001 |
| JP | 2005-162841 | | 6/2005 |
| JP | 2006-061038 | | 3/2006 |
| JP | 2011-503186 | | 1/2011 |
| JP | 2014-218447 | | 11/2014 |
| WO | 2009/064480 | | 5/2009 |
| WO | 2013/180246 | | 12/2013 |
| WO | 2013/180248 | | 12/2013 |
| WO | 2013/180249 | | 12/2013 |
| WO | 2014/046035 | | 3/2014 |
| WO | 2016/203009 | A1 | 12/2016 |
| WO | 2018/021265 | | 2/2018 |

OTHER PUBLICATIONS

Supplementary European Search Report issued in EP Patent Application No. 19951729.3, Oct. 28, 2022.
International Search Report issued with respect to Patent application PCT/JP2019/043581, dated Dec. 10. 2019, with English translation.
Written Opinion of the International Searching Authority issued in International Application No. PCT/JP2019/043581, dated Dec. 10, 2019, along with an English translation thereof.

\* cited by examiner

*Primary Examiner* — Robert A Wax
*Assistant Examiner* — Andre Mach
(74) *Attorney, Agent, or Firm* — GREENBLUM & BERNSTEIN, P.L.C.

(57) ABSTRACT

A cellulose composition containing cellulose, glucose and sorbitol, wherein a total content of glucose and sorbitol is 0.7 mg or more and 4.0 mg or less per 5 g of the cellulose composition. A tablet contains the cellulose composition. An orally disintegrating tablet contains the cellulose composition.

8 Claims, No Drawings

CELLULOSE COMPOSITION, TABLET, AND ORALLY DISINTEGRATING TABLET

TECHNICAL FIELD

The present invention relates to a cellulose composition, a tablet and an orally disintegrating tablet.

BACKGROUND ART

Conventionally, in the fields of pharmaceutical products, health foods, food products and other chemical industries, it is widely known that a cellulose powder is used as an excipient to prepare a molded product, for example, a tablet or the like which contains an active ingredient. In particular, orally disintegrating tablets that can be taken without water have become the mainstream of recent tablets, and are a dosage form that has greatly developed in the field of pharmaceutical formulations. In recent years, although orally disintegrating tablets have also been produced by the same production method as that of conventional tablets, which is not a special production method, the production method is originally based on the technology established by making full use of the blending ratio of various additives and excipients in order to obtain practical tablet hardness and satisfactory disintegration properties and administration feeling as orally disintegrating tablets. Formulations based on such technology are becoming important as high-value-added formulations, not only for improving the quality of life (QOL) of patients, but also for the product life cycle management (PLCM) of the products. Furthermore, in the rapidly aging society, the orally disintegrating tablet which rapidly disintegrates with saliva or a small amount of water greatly contributes to the improvement of adherence and compliance, such as the convenience and the ease of administration to patients in a medical setting, as a dosage form that can be easily taken even by patients with weak swallowing ability such as the elderly and children. However, the history of orally disintegrating tablets is short, and there are also technical problems such as the disintegration time and administration feeling in the oral cavity, and the securing of hardness for tablets that do not crack or wear during production or distribution.

Patent Document 1 discloses a cellulose powder having an average degree of polymerization of 100 or more and 350 or less, a weight average particle size of more than 30 µm and 250 µm or less, an apparent specific volume of 2 cm$^3$/g or more and less than 15 cm$^3$/g, and a particle size distribution sharpness of 1.5 or more and 2.9 or less. It is disclosed that by using this cellulose powder, it has the effect of improving the compression moldability, uniformly retaining sticky and hygroscopic Chinese herbal medicines and viscous components, sharpening the particle size distribution of granules as a result of sharpening the particle size distribution of the cellulose powder, shortening the disintegration time, and imparting stable disintegration properties over time.

However, Patent Document 1 is based on the assumption that a pure cellulose powder is used, and there is room for improvement as a composition containing cellulose in view of the disintegration properties and storage stability required for an orally disintegrating tablet.

PRIOR ART LITERATURE

Patent Document

Patent Document 1: International Patent Publication No. 2013/180248

SUMMARY OF INVENTION

Problems to be Solved by the Invention

The present invention has been made in view of the above circumstances, and provides a cellulose composition capable of obtaining a tablet having excellent storage stability while maintaining disintegration properties as an orally disintegrating tablet in a favorable manner, a tablet and an orally disintegrating tablet containing the aforementioned cellulose composition.

Means for Solving the Problems

That is, the present invention includes the following aspects.

(1) A cellulose composition containing cellulose, glucose and sorbitol, wherein a total content of glucose and sorbitol is 0.7 mg or more and 4.0 mg or less per 5 g of the aforementioned cellulose composition.

(2) The cellulose composition according to (1), wherein a content of a water-soluble substance is 2.5 mg or more and 12.5 mg or less per 5 g of the aforementioned cellulose composition.

(3) The cellulose composition according to (1) or (2), wherein a content of glucose is 0.3 mg or more and 4.0 mg or less per 5 g of the aforementioned cellulose composition.

(4) The cellulose composition according to any one of (1) to (3), wherein a content of sorbitol is 0.2 mg or more and 4.0 mg or less per 5 g of the aforementioned cellulose composition.

(5) The cellulose composition according to any one of (1) to (4), wherein the aforementioned cellulose composition is a powder, and an average particle size of the powder is 10 µm or more and 200 µm or less.

(6) The cellulose composition according to any one of (1) to (5), wherein a water absorption rate is 2.0 g$^2$/s or more and 9.0 g$^2$/s or less.

(7) A tablet containing the cellulose composition according to any one of (1) to (6).

(8) An orally disintegrating tablet containing the cellulose composition according to any one of (1) to (6).

Effects of the Invention

According to the cellulose composition of the above aspect, it is possible to provide a cellulose composition capable of obtaining a tablet having excellent storage stability while maintaining disintegration properties as an orally disintegrating tablet in a favorable manner. The tablet and the orally disintegrating tablet of the above aspect contain the aforementioned cellulose composition, exhibit favorable disintegration properties as orally disintegrating tablets, and are excellent in storage stability.

EMBODIMENTS FOR CARRYING OUT THE INVENTION

Hereinafter, an embodiment for carrying out the present invention (hereinafter, simply referred to as "the present embodiment") will be described in detail. It should be noted that the present invention is not limited to the following embodiments, and can be variously modified and implemented within the scope of the gist thereof.

<Cellulose Composition>

A cellulose composition of the present embodiment contains cellulose, glucose and sorbitol. The total content of monosaccharides, that is, glucose and sorbitol per 5 g of the aforementioned cellulose composition is 0.7 mg or more and 4.0 mg or less, preferably 1.0 mg or more and 3.5 mg or less, and more preferably 2.0 mg or more and 3.0 mg or less.

When the content of monosaccharides per 5 g of the cellulose composition is within the above range, the disintegration properties can be improved when formed into an orally disintegrating tablet. In addition, the storage stability can be improved when formed into a tablet. It should be noted that when the cellulose composition is a powder, it is desirable that a single particle contains cellulose, glucose and sorbitol.

Conventionally, from the viewpoint of quality assurance, pharmaceutical additives or food additives have been required to have high purity, and conventional cellulose powders used as pharmaceutical additives are pure cellulose of extremely high purity. On the other hand, the cellulose composition of the present embodiment may contain a water-soluble substance which has been conventionally excluded as an impurity within a specific range. This water-soluble substance is mainly composed of monosaccharides such as glucose and sorbitol, and cellooligosaccharides such as cellobiose, cellotriose, cellotetraose, cellopentaose, cellohexaose and celloheptaose. Among these constituents, by containing glucose and sorbitol as monosaccharides within specific ranges, it is possible to effectively suppress the occurrence of remaining core (core residue) when formed into an orally disintegrating tablet, and to improve the disintegration properties.

In the cellulose composition of the present embodiment, the content of the water-soluble substance per 5 g of the cellulose composition is preferably 2.5 mg or more and 12.5 mg or less, more preferably 3.0 mg or more and 12.0 mg or less, still more preferably 3.5 mg or more and 11.5 mg or less, and particularly preferably 4.0 mg or more and 11.0 mg or less.

When the water-soluble substance in the cellulose composition is within the above range, it is possible to suppress the occurrence of core residue when formed into an orally disintegrating tablet, and the disintegration properties can be improved.

In the cellulose composition of the present embodiment, the glucose content per 5 g of the cellulose composition is preferably 0.3 mg or more and 4.0 mg or less, more preferably 0.5 mg or more and 3.5 mg or less, and still more preferably 1.0 mg or more and 3.0 mg or less.

When the glucose content in the cellulose composition is within the above range, it is possible to suppress the occurrence of core residue when formed into an orally disintegrating tablet, and the disintegration properties can be improved. In addition, the reaction between the active ingredient and glucose contained in the tablet can be suppressed, and as a result, the storage stability can be improved when formed into a tablet.

In the cellulose composition of the present embodiment, the sorbitol content per 5 g of the cellulose composition is preferably 0.2 mg or more and 4.0 mg or less, more preferably 0.3 mg or more and 3.5 mg or less, still more preferably 0.5 mg or more and 3.5 mg or less, and particularly preferably 1.0 mg or more and 3.0 mg or less.

When the sorbitol content in the cellulose composition is within the above range, it is possible to suppress the occurrence of core residue when formed into an orally disintegrating tablet, and the disintegration properties can be improved. In addition, the reaction between the active ingredient and sorbitol contained in the tablet can be suppressed, and as a result, the storage stability can be improved when formed into a tablet.

Glucose and sorbitol are both monosaccharides having similar properties, but sorbitol tends to be superior in terms of disintegration properties and storage stability as an orally disintegrating tablet. Therefore, it is preferable to contain more sorbitol than glucose.

The contents of glucose and sorbitol in the cellulose composition are measured by liquid chromatography/mass spectrometry (LC/MS) as shown in Examples described later. It should be noted that if other components whose peaks easily overlap with the peaks attributed to glucose and sorbitol are contained, first, the conditions of liquid chromatography are appropriately adjusted to verify whether peak separation is possible. If peak separation is impossible, a peak area derived from glucose and sorbitol can be determined using an extracted ion chromatogram of the base peak ion derived from glucose and sorbitol in mass spectrometry.

The contents of glucose and sorbitol in the cellulose composition can also be adjusted, for example, by adding an appropriate amount of at least one of glucose and sorbitol during the production process of the cellulose composition. There is a possibility that the contents of glucose and sorbitol can be controlled depending on the selection of raw materials of the cellulose composition and the production conditions, but in order to control them within the desired content ranges, a method of adding an appropriate amount during the production process is simple and preferable.

The cellulose composition of the present embodiment preferably has a water absorption rate of 2.0 $g^2$/s or more and 9.0 $g^2$/s or less, more preferably 2.2 $g^2$/s or more and 8.2 $g^2$/s or less, still more preferably 3.0 $g^2$/s or more and 8.0 $g^2$/s or less, particularly preferably 3.4 $g^2$/s or more and 7.4 $g^2$/s or less, and most preferably 3.4 $g^2$/s or more and 7.2 $g^2$/s or less.

When the water absorption rate is within the above range, the occurrence of core residue can be suppressed more effectively when formed into an orally disintegrating tablet, and the disintegration properties can be further improved.

It should be noted that the water absorption rate can be measured using a Peneto Analyzer (model: PNT-N, manufactured by Hosokawa Micron Corporation) as shown in Examples described later.

<Form of Cellulose Composition>

The cellulose composition in the present embodiment is preferably in any form of a powder, granule, paste, or wet cake. From the viewpoint of handleability, a cellulose powder is preferable. The cellulose powder is generally referred to as crystalline cellulose, powdered cellulose or the like, and is suitably used as a pharmaceutical additive or a food additive. Crystalline cellulose is preferable as the cellulose powder. As the crystalline cellulose, for example, the microcrystalline cellulose defined by the Joint FAO/WHO Expert Committee on Food Additives(JECFA), the microcrystalline cellulose described in the 8th edition of Japan's Specifications and Standards for Food Additives (issued by the Ministry of Health, Labour and Welfare, Japan), the crystalline cellulose described in the 17th revised Japanese Pharmacopoeia, and the crystalline cellulose described in the United States Pharmacopeia, the European Pharmacopoeia and the like are known.

It should be noted that from the viewpoint of improving the balance between moldability, fluidity and disintegration properties, an average degree of polymerization of cellulose in the cellulose composition is preferably 400 or less, and more preferably 350 or less. The lower limit value of the average degree of polymerization is preferably 100 or more. The average degree of polymerization of cellulose can be measured by a copper ethylenediamine solution viscosity method described in the identification test (3) for crystalline cellulose or the identification test (3) for powdered cellulose in Japanese Pharmacopoeia.

<Preferred Form as Cellulose Powder>

When the cellulose composition of the present embodiment is a powder, the average particle size of the powder is preferably 10 μm or more and 200 μm or less, more preferably 15 μm or more and 90 μm or less, still more preferably 20 μm or more and 80 μm or less, particularly preferably 30 μm or more and 70 μm or less, and most preferably 40 μm or more and 60 μm or less.

When the average particle size is equal to or less than the above upper limit value, it is easy to be uniformly mixed with an active ingredient such as a drug, and the disintegration properties improve when formed into an orally disintegrating tablet. On the other hand, when the average particle size is equal to or more than the above lower limit value, the handleability improves.

It should be noted that the average particle size of the cellulose powder is a particle size at a cumulative volume of 50% measured by a laser diffraction type particle size distribution meter (model: LA-950 V2 (product name), manufactured by Horiba Ltd.).

When the cellulose composition of the present embodiment is a powder, the loose bulk density is preferably 0.10 g/mL or more and 0.35 g/mL or less, more preferably 0.11 g/mL or more and 0.30 g/mL or less, and still more preferably 0.13 g/mL or more and 0.28 g/mL or less.

When the loose bulk density is equal to or more than the above lower limit value, the compression moldability can be further improved. On the other hand, when the loose bulk density is equal to or less than the above upper limit value, the loadability further improves.

The loose bulk density can be measured by using a method described in Examples described later.

When the cellulose composition of the present embodiment is a powder, the packed bulk density is preferably 0.27 g/mL or more and 0.50 g/mL or less, more preferably 0.28 g/mL or more and 0.48 g/mL or less, and still more preferably 0.28 g/mL or more and 0.44 g/mL or less.

When the packed bulk density is equal to or more than the above lower limit value, it is easy to be uniformly mixed with an active ingredient such as a drug, and the handleability further improves. On the other hand, when the packed bulk density is equal to or less than the above upper limit value, the occurrence of segregation due to the density difference with the particles of the active ingredient or other additives can be suppressed more effectively.

The packed bulk density can be measured by using a method described in Examples described later.

Further, when the loose bulk density and the packed bulk density simultaneously satisfy the above-mentioned ranges, the tablets obtained by compression molding tend to exhibit excellent moldability and disintegration properties.

When the cellulose composition of the present embodiment is a powder, the compression rate is preferably 22% or more and 58% or less, more preferably 30% or more and 55% or less, and still more preferably 35% or more and 50% or less.

When the compression rate is within the above range, the fluidity of the cellulose powder itself further improves, and the occurrence of segregation can be suppressed more effectively.

The compression rate can be calculated by using a method described in Examples described later.

When the cellulose composition of the present embodiment is a powder, a ratio of the major axis with respect to the minor axis of the cellulose particles, that is, the aspect ratio (L/D) is preferably 1.6 or more and 3.8 or less, more preferably 2.0 or more and 3.6 or less, and still more preferably 2.3 or more and 3.3 or less.

When the aspect ratio is within the above range, the miscibility with the active ingredient also improves, the entanglement between elongated particles is appropriate, and the balance between moldability and disintegration properties is excellent.

The aspect ratio (L/D) can be measured by using a method described in Examples described later.

<Method for Producing Cellulose Composition>

An example of a method for producing the cellulose composition of the present embodiment will be described below. However, the cellulose composition of the present embodiment is not limited to those obtained by the following production method.

The cellulose composition of the present embodiment can be obtained, for example, by a method including a step of dispersing a hydrolyzed natural cellulose-based substance in an appropriate medium to obtain an aqueous cellulose dispersion, and a step of drying the aqueous dispersion. The solid content concentration of the aqueous cellulose dispersion is not particularly limited, and can be, for example, 1% by mass or more and 30% by mass or less. In this case, it is also possible to isolate a solid content containing the hydrolyzed cellulose-based substance from a hydrolysis reaction solution obtained by a hydrolysis treatment, and to dry a dispersion prepared by separately dispersing this solid content in an appropriate medium. Further, glucose or sorbitol may be added to and mixed with the cellulose dispersion so that the contents of glucose and sorbitol in the cellulose composition are within specific ranges, followed by drying. In addition, when the above hydrolysis solution forms a cellulose dispersion as it is, the dispersion can also be directly dried.

The natural cellulose-based substance may be of vegetable or animal origin, and is, for example, a fibrous material derived from a natural product containing cellulose such as wood, bamboo, cotton, ramie, sea squirt, bagasse, kenaf and bacterial cellulose, and preferably has a cellulose I crystal structure. As the raw material, one of the above-mentioned natural cellulose-based substances may be used, or a mixture of two or more types thereof may be used. Further, it is preferably used in the form of refined pulp, but a method for refining the pulp is not particularly limited, and any of the dissolving pulp, kraft pulp, needle bleached kraft pulp (NBKP) and the like may be used.

In the above-mentioned production method, water is preferable as the medium used when the solid content containing the natural cellulose-based substance is dispersed in an appropriate medium, but there is no particular limitation as long as it is industrially used, and for example, an organic solvent may be used. Examples of the organic solvent include alcohols such as methanol, ethanol, isopropyl alcohol, butyl alcohol, 2-methylbutyl alcohol and benzyl alcohol; hydrocarbons such as pentane, hexane, heptane and cyclohexane; and ketones such as acetone and ethyl methyl ketone. In particular, the organic solvent is preferably a solvent used in pharmaceutical products, and examples thereof include those classified as solvents in "Japanese Pharmaceutical Excipients Directory 2016" (published by Yakuji Nippo, Ltd.). Any one of water and the organic solvents may be used alone, two or more types thereof may be used in combination, or the solid content may be dispersed once in one medium and then dispersed in a different medium after removing the initial medium.

For example, pulp fibers having an average width of 2 μm or more and 30 μm or less and an average thickness of 0.5 μm or more and 5 μm or less are hydrolyzed while stirring under pressure at a temperature of 70° C. or higher and 140° C. or lower in a hydrochloric acid of 0.01% by mass or more and 1.0% by mass or less. The degree of progress of hydrolysis can be controlled by adjusting the motor power (P: unit W) and stirring capacity (L: unit L) of the stirrer. For example, by adjusting the P/V ratio represented by the following formula, it is possible to control the average particle size of the finally obtained cellulose particles to 200 μm or less.

$$P/V(W/L) = [\text{actual motor power}(W) \text{ of stirrer}]/[\text{stirring capacity}(L)]$$

A drying method for drying the aqueous cellulose dispersion to obtain the cellulose composition is not particularly limited. For example, any method of freeze drying, spray drying, drum drying, shelf drying, flash drying and vacuum drying may be used, and one of these methods may be used alone, or two or more types thereof may be used in combination. A spraying method for spray drying may be any spraying method of a disc type, pressure nozzle type, two fluid pressure nozzle type, four fluid pressure nozzle type and the like, and one of these methods may be used alone, or two or more types thereof may be used in combination.

At the time of the above spray drying process, a trace amount of a water-soluble polymer and a surfactant may be added for the purpose of lowering the surface tension of the dispersion liquid, and a foaming agent or gas may be added to the dispersion liquid for the purpose of accelerating the vaporization rate of the medium.

By controlling the acid concentration and stirring conditions when preparing the aqueous cellulose dispersion, an aqueous cellulose dispersion containing dispersed cellulose particles having a specific average particle size can be obtained, and furthermore, the average particle size and compression rate of the obtained cellulose composition can be controlled by adjusting the solid content concentration and the drying conditions of the aqueous cellulose dispersion when drying the aqueous cellulose dispersion. For example, when the aqueous cellulose dispersion is dried by a disc-type spray drying, by setting the stirring power within a specific range when preparing the aqueous cellulose dispersion, and setting conditions of the solid content concentration of the aqueous cellulose dispersion and the number of revolutions in the disc type spray drying within specific ranges at the time of spray drying, a cellulose composition having an average particle size and compression rate within specific ranges can be obtained.

Further, as described in Examples described later, a cellulose composition in which the contents of glucose and sorbitol in the cellulose composition are within specific ranges may be obtained by adding and mixing glucose and sorbitol with the aqueous cellulose dispersion, and drying the resulting mixture as necessary.

When the cellulose composition is dried and formed into a powder, even if the average particle size is greater than 200 μm, the average particle size can be adjusted to 10 μm or more and 200 μm or less by subjecting the composition to a pulverization step described later.

The pulverization step can be carried out by pulverizing the dried cellulose composition with a pulverizer such as an ultracentrifugal mill (ZM-200, manufactured by Retsch GmbH), a jet mill (STJ-200, manufactured by Seishin Enterprise Co., Ltd.), a hammer mill (H-12, manufactured by Hosokawa Micron Corporation), a bantam mill (AP-B, manufactured by Hosokawa Micron Corporation), a pin mill (160Z, manufactured by Powrex Corporation), a feather mill (FM, manufactured by Hosokawa Micron Corporation), a hammer mill (HM-600, manufactured by Nara Machinery Co., Ltd.), a flash mill (FL-250N, manufactured by Dalton Corporation), a ball mill (Emax, manufactured by Retsch GmbH), a vibrating ball mill (2C, manufactured by TRU), and a screen mill for passing through a screen (U30, manufactured by Powrex Corporation). In particular, a jet mill pulverizer (STJ-200, manufactured by Seishin Enterprise Co., Ltd.) is preferable because it is an air flow type pulverizer that pulverizes particles while colliding them with each other at a high air pressure, and secondary particles are easily pulverized into primary particles.

As for the pulverization conditions of the jet mill pulverizer, the amount of powder supply and the pulverizing pressure are important, and when the jet mill pulverizer (STJ-200, manufactured by Seishin Enterprise Co., Ltd.) is used, the supplied amount is preferably 10 kg/hour or more and 20 kg/hour or less, and more preferably 15 kg/hour or more and 20 kg/hour or less. Further, the pulverizing pressure is preferably 0.15 MPa or more and 0.70 MPa or less, and more preferably 0.30 MPa or more and 0.50 MPa or less. When the amount of powder supply and the pulverizing pressure are within the above ranges, the average particle size tends to be easily controlled to 10 μm or more and 200 μm or less.

Even when the average particle size of the cellulose powder after drying is less than 100 μm, the average particle size of the cellulose powder can be adjusted to a desired range of about 100 μm or more and 200 μm or less by employing a granulation method such as stirring granulation and fluidized bed granulation.

<Intended Use>

By blending the cellulose composition of the present embodiment with a composition containing an active ingredient, it is possible to obtain a tablet having excellent storage stability while maintaining disintegration properties in a favorable manner. As shown in Examples described later, the cellulose composition of the present embodiment is excellent in disintegration properties when formed into an orally disintegrating tablet, and is therefore suitably used as an excipient for an orally disintegrating tablet.

Hereinafter, a composition for tableting which contains one or more active ingredients and the cellulose composition of the present embodiment is referred to as a "composition of the present embodiment".

Although the blending ratio of the above cellulose composition with respect to the composition of the present embodiment can be any ratio, 90% by mass or less with respect to the total mass of the tablet is a practically preferable range. The lower limit value is practically 0.1% by mass. When used in tablets containing a large amount of active ingredient, it can be set to about 0.1% by mass or more and 50% by mass or less.

Suitable active ingredients contained in the composition of the present embodiment are exemplified below.

As the medicinal ingredient of a pharmaceutical product, an active ingredient of an orally administered pharmaceutical product is preferable. Examples of the orally administered pharmaceutical product include antipyretic analgesic antiphlogistics, sedative hypnotics, drugs for sleepiness prevention, antivertiginous drugs, pediatric analgesics, stomachics, antacids, digestives, cardiotonics, antiarrhythmic drugs, depressors, vasodilators, diuretics, antiulcer drugs, intestinal drugs, drugs for treatment of osteoporosis, antitussive expectorants, antiasthmatics, antimicrobial agents, pollakiuria improving agents, analeptics and vitamin pills. One of these medicinal ingredients may be used alone, or two or more types thereof may be used in combination.

Specific examples thereof include the medicinal ingredients of pharmaceutical products listed in "Japanese Pharmacopoeia", "The Japanese Pharmaceutical Codex (JPC)", "the United States Pharmacopeia (USP)", "the National Formulary (NF)" and "European Pharmacopoeia (EP)", such as aspirin, aspirin aluminum, acetaminophen, ethenzamide, sazapyrin, salicylamide, lactyl phenetidine, isotibenzyl hydrochloride, diphenylpyraline hydrochloride, diphenhydramine hydrochloride, dipherol hydrochloride, riprolidine hydrochloride, tryperenamine hydrochloride, tonzilamine hydrochloride, fenetazine hydrochloride, metodirazine hydrochloride, diphenhydramine salicylate, carbinoxamine diphenyldisulfonate, alimemazine tartrate, diphenhydramine tannate, diphenylpyraline theocrate, mebhydrolin napadisylate, promethazine methylene disalicylate, carbinoxamine maleate, dl-chlorpheniramine maleate, d-chlorpheniramine maleate, dipherol phosphate, alloclamide hydrochloride, cloperastin hydrochloride, pentoxiberin citrate (carbetapentane citrate), tipepidine citrate, sodium dibunato, dextromethorphan hydrobromide, dextromethorphan phenolphthalic acid, tipepidine hibenzate, cloperastin fendyzoate, codeine phosphate, dihydrocodeine phosphate, noscapine hydrochloride, noscapine, dl-methylephedrine hydrochloride, dl-methylephedrine saccharin salt, potassium guaiacol sulfonate, guaifenesin, sodium benzoate caffeine, caffeine, anhydrous caffeine, vitamin B1 and its derivatives and their salts, vitamin B2 and its derivatives and their salts, vitamin C and its derivatives and their salts, hesperidin and its derivatives and their salts, vitamin B6 and its derivatives and their salts, nicotinamide, calcium pantothenate, amino acetate, magnesium silicate, synthetic aluminum silicate, synthetic hydrotalcite, magnesium oxide, dihydroxyaluminum aminoacetate (aluminum glycinate), aluminum hydroxide gel (as dry aluminum hydroxide gel), dry aluminum hydroxide gel, aluminum hydroxide/magnesium carbonate mixed dry gel, aluminum hydroxide/sodium hydrogen carbonate coprecipitation product, aluminum hydroxide/calcium carbonate/magnesium carbonate coprecipitation product, magnesium hydroxide/potassium aluminum sulfate coprecipitation product, magnesium carbonate, magnesium aluminate metasilicate, ranitidine hydrochloride, cimetidine, famotidine, naproxen, diclophenac sodium, piroxicam, azulene, indomethacin, ketoprofen, ibuprofen, diphenidol hydrochloride, diphenylpyraline hydrochloride, diphenhydramine hydrochloride, promethazine hydrochloride, meclizine Hydrochloride, dimenhydrinate, diphenhydramine tannate, fenetazine tannate, diphenylpyraline theocrate, diphenhydramine fumarate, promethazine methylene disalicylate, scopolamine hydrobromide, oxyphencyclimine hydrochloride, dicycloverine hydrochloride, metixene hydrochloride, methylatropine bromide, methylanisotropin bromide, methylscopolamine bromide, methyl-1-hyoscyamine bromide, methyl benactidium bromide, belladonna extract, isopropamide iodide, diphenylpiperidinomethyldioxolane iodide, papaverine hydrochloride, aminobenzoic acid, cesium oxalate, ethyl piperidylacetylaminobenzoate, aminophylline, diprophylline, theophylline, sodium bicarbonate, fursultiamine, isosorbide nitrate, ephedrine, cephalexin, ampicillin, sulfisoxazole, sucralfate, allyl isopropyl acetyl urea, bromvalerylurea or the like, ephedra, nandina fruit, cherry tree bark, polygala root, licorice, platycodon grandiflorum, plantago seed, senega, fritillaria bulb, fennel, phellodendron bark, coptis rhizome, curcuma rhizome, chamomile, cinnamon, gentiana, oriental bezoar, beast gall (including bear's gall), ladybells, ginger, atractylodes lancea rhizome, clove, citrus unshiu peel, atractylodes rhizome, earthworm, panax rhizome, ginseng, valerian, moutan bark, Japanese zanthoxylum peel and extracts thereof; insulin, vasopressin, interferon, urokinase, serratiopeptidase, somatostatin and the like. One of these medicinal ingredients selected from the above list may be used alone, or two or more types thereof may be used in combination.

The active ingredient for health foods is not limited as long as it is an component blended for the purpose of enhancing health, and examples thereof include powdered green juice, aglycone, agaricus, ashwagandha, astaxanthin, acerola, amino acids (valine, leucine, isoleucine, lysine, methionine, phenylalanine, threonine, tryptophan, histidine, cystine, tyrosine, arginine, alanine, aspartic acid, powdered seaweed, glutamine, glutamic acid, glycine, proline, serine and the like), alginic acid, *Ginkgo biloba* extract, sardine peptides, turmeric, uronic acid, echinacea, Siberian ginseng, oligosaccharides, oleic acid, nucleoproteins, dried skipjack peptides, catechin, potassium, calcium, carotenoid, garcinia cambogia, L-carnitine, chitosan, conjugated linoleic acid, Aloe arborescens, Gymnema sylvestre extract, citric acid, Orthosiphon stamineus, glycerides, glycenol, glucagon, curcumin, glucosamine, L-glutamine, chlorella, cranberry extract, Uncaria tomentosa, germanium, enzymes, Korean ginseng extract, coenzyme Q10, collagen, collagen peptides, coleus blumei, chondroitin, powdered psyllium husks, Crataegi fructus extract, saponin, lipids, L-cystine, Japanese basil extract, citrimax, fatty acids, phytosterol, seed extract, spirulina, squalene, Salix alba, ceramide, selenium, St. John's wort extract, soy isoflavone, soy saponin, soy peptides, soy lecithin, monosaccharides, proteins, chaste tree extract, iron, copper, docosahexaenoic acid, tocotrienol, nattokinase, Bacillus natto culture extract, sodium niacin, nicotine acid, disaccharides, lactic acid bacterium, garlic, saw palmetto, sprouted rice, pearl barley extract, herb extract, valerian extract, pantothenic acid, hyaluronic acid, biotin, chromium picolinate, vitamin A, vitamin A2, vitamin B1, vitamin B2, vitamin B6, vitamin B12, vitamin C, vitamin D, vitamin E, vitamin K, hydroxytyrosol, bifidobacterium, beer yeast, fructo oligosaccharides, flavonoid, Butcher's broom extract, black cohosh, blueberry, prune concentrate, proanthocyanidin, proteins, propolis, bromelain, probiotics, phosphatidylcholine, phosphatidylserine, β-carotene, peptides, safflower extract, Grifola frondosa extract, maca extract, magnesium, milk thistle, manganese, mitochondria, mineral, mucopolysaccharides, melatonin, Fomes yucatensis, powdered melilot extract, molybdenum, vegetable powder, folic acid, lactose, lycopene, linolic acid, lipoic acid, phosphorus, lutein, lecithin, rosmarinic acid, royal jelly, DHA and EPA.

The active ingredient may be water-soluble or poorly soluble in water. The expression "poorly soluble in water"

means that the amount of water required for dissolving 1 g of a solute is 30 mL or more as defined in the 17th revised Japanese Pharmacopoeia.

Examples of the solid active ingredient poorly-soluble in water include the medicinal ingredients of pharmaceutical product described in "Japanese Pharmacopeia", "JPC", "USP", "NF" and "EP", including antipyretic analgesics, drugs for the nervous system, hypnotics and sedatives, muscle relaxants, hypotensive agent, antihistamines and the like, such as acetaminophen, ibuprofen, benzoic acid, ethenzamide, caffeine, camphor, quinine, calcium gluconate, dimercaprol, sulfamine, theophylline, theobromine, riboflavin, mephenesin, phenobarbital, aminophyllin, thioacetazone, quercetin, rutin, salicylic acid, theophylline sodium salt, pyrapital, quinine hydrochloride, irgapyrin, digitoxin, griseofulvin and phenacetin; antibiotics such as acetylspiramycin, ampicillin, erythromycin, kitasamycin, chloramphenicol, triacetyloleandomycin, nystatin, and colistin sulfate; steroid hormones such as methyltestosterone, methylandrostetronediol, progesterone, estradiol benzoate, ethynyl estradiol, deoxycorticosterone acetate, cortisone acetate, hydrocortisone, hydrocortisone acetate and prednisolone; non-steroidal estrogen hormones such as dienestrol, hexastrol, diethylstilbestrol, diethylstilbestrol dipropionate and chlorotrianisene; and other fat-soluble vitamins. One of these active ingredients selected from the above list may be used alone, or two or more types thereof may be used in combination. If the active ingredient is poorly soluble in water, the effects of the present invention can be obtained by blending it as an active ingredient in the composition of the present embodiment regardless of the degree of sublimation and surface polarity.

The active ingredient may be a poorly water-soluble oil or liquid. Examples of the poorly water-soluble oily or liquid active ingredient include the medicinal ingredients of pharmaceutical products described in "Japanese Pharmacopoeia", "JPC", "USP", "NF", or "EP", including vitamins such as teprenone, indomethacin farnesyl, menatetrenone, phytonadione, vitamin A oil, fenipentol, vitamin D and vitamin E; higher unsaturated fatty acids such as docosahexaenoic acid (DHA), eicosapentaenoic acid (EPA) and cod liver oil; coenzyme Qs; and oil-soluble flavorings such as orange oil, lemon oil and peppermint oil. Although there are various homologues and derivatives of vitamin E, there is no particular limitation as long as it is in a liquid form at room temperature. Examples thereof include dl-α-tocopherol, dl-α-tocopherol acetate, d-α-tocopherol and d-α-tocopherol acetate. One of these selected from the above list may be used alone, or two or more types thereof may be used in combination.

The active ingredient may be a semi-solid active ingredient poorly soluble in water. Examples of the semi-solid active ingredient poorly-soluble in water include Chinese herbal medicines or crude drug extracts such as earthworm, licorice, cassia bark, peony root, moutan bark, Japanese valerian, zanthoxylum fruit, ginger, citrus unshiu peel, ephedra herb, nandina fruit, yellow bark, polygala root, platycodon root, plantago seed, plantago herb, shorttube lycoris, senega root, fritillaria bulb, fennel, phellodendron bark, coptis rhizome, zedoary, matricaria, gentian, oriental bezoar, beast gall, adenophorae radix, ginger, atractylodes lancea rhizome, clove, citrus unshiu peel, atractylodes rhizome, panax rhizome, ginseng, kakkonto, keihito, kousosan, saikokeishito, shosaikoto, shoseiryuto, bakumondoto, hangekobokuto and maoto; an oyster meat extract, propolis or extract thereof, and coenzyme Qs. One of these active ingredients selected from the above list may be used alone, or two or more types thereof may be used in combination.

The active ingredient may be a sublimable active ingredient. Examples of the sublimable active ingredient include sublimable medicinal ingredients of pharmaceutical products described in "Japanese Pharmacopoeia", "JPC", "USP", "NF", or "EP", such as benzoic acid, ethenzamide, caffeine, camphor, salicylic acid, phenacetin and ibuprofen. One of these active ingredients selected from the above list may be used alone, or two or more types thereof may be used in combination. It should be noted that the sublimable active ingredient referred to in the present specification is not particularly limited as long as it has sublimation properties, and it may be in any state of solid, liquid or semi-solid at room temperature.

Further, as the active ingredient, a medicinal ingredient having a small maximum blending quantity per tablet can also be preferably used.

Examples of the medicinal ingredient having a small maximum blending quantity per tablet include the following medicinal ingredients having a maximum blending quantity per tablet of 100 mg or less, or 10 mg or less.

Examples of medicinal ingredients having a maximum blending quantity of more than 100 mg per tablet include abacavir, acetazolamide, acetylsalicylic acid, aciclovir, albendazole, aliskiren fumarate, allopurinol, amiodarone, amodiaquine, amoxicillin, aprepitant, artemether, artesunate, atazanavir, calcium, capecitabine, carbamazepine, carbidopa, cefalexin, cefixime, celecoxib, chloroquine, ciprofloxacin, clarithromycin, potassium clavulanate, clopidogrel, clozapine, cycloserine, darunavir, darunavir ethanolate, dasabuvir, dasatinib, deferasirox, dihydroartemisinin piperaquine phosphate, diloxanide, efavirenz, emtricitabine, erlotinib hydrochloride, ethambutol, ethionamide, famciclovir, gefitinib, griseofulvin, hydroxycarbamide, hydroxychloroquine, ibuprofen, imatinib, irbesartan, isoniazid, lamivudine, lamotrigine, lanthanum carbonate hydrate, ledipasvir, levamisole, levetiracetam, levodopa, levofloxacin, linezolid, lithium carbonate, lopinavir, lumefantrine, mebendazole, mefloquine, mesna, metformin, methyldopa, metronidazole, morphine, moxifloxacin, nevirapine, niclosamide, nifurtimox, ombitasvir, p-aminosalicylic acid, paracetamol, paritaprevir, penicillamine, pentamidine, phenoxymethylpenicillin, pirfenidone, praziquantel, pyrantel, pyrazinamide, pyronaridine tetraphosphate, quinine, raltegravir, ranitidine, ribavirin, rifampicin, rifapentine, sevelamer hydrochloride, sofosbuvir, sorafenib tosilate, sulfadiazine, sulfamethoxazole, sulfasalazine, tenofovir, tenofovir disoproxil fumarate, triclabendazole, trimethoprim, valganciclovir, valproic acid, velpatasvir, sodium valproate, voriconazole and zidovudine.

Examples of medicinal ingredients having a maximum blending quantity of more than 10 mg and 100 mg or less per tablet include aripiprazole, artesunate, ascorbic acid, azathioprine, bazedoxifene acetate, bicalutamide, calcium folinate hydrate, clomiphene, cyclizine, cyclophosphamide, dasatinib hydrate, delamanid, dolutegravir, eletriptan hydrobromide, febuxostat, fluoxetine, furosemide, galantamine hydrobromide, hydralazine, hydrochlorothiazide, hydrocortisone, memantine hydrochloride, mercaptopurine, midazolam, miltefosine, minodronic acid hydrate, mirtazapine, neostigmine, nicotinamide, olmesartan medoxomil, omeprazole, ondansetron, pancrelipase, potassium iodide, prednisolone, primaquine, pyrimethamine, propranolol, propylthiouracil, pyridoxine, simvastatin, sitafloxacin hydrate, spironolactone, tadalafil, tamoxifen, thiamine, thioguanine, tolvaptan, ulipristal, vardenafil hydrochloride hydrate, zinc sulfate, acotiamide hydrochloride hydrate, amitriptyline, bedaquiline, benznidazole, bosentan hydrate, chlorpromazine, cinacalcet hydrochloride, daclatasvir, dapsone, diethylcarbamazine, doxycycline, entacapone, eplerenone, ferrous sulfate hydrate, gliclazide, ibandronate sodium hydrate, losartan, miglitol, nitrofurantoin, phenobarbital, phenytoin, pyridostigmine, raloxifene hydrochloride, ritonavir, succimer, telmisartan, topiramate and verapamil.

Examples of medicinal ingredients having a maximum blending quantity of 10 mg or less per tablet include anastrozole, dienogest, digoxin, dutasteride, entecavir, entecavir hydrate, ethinylestradiol, finasteride, fludrocortisone, glyceryl trinitrate, imidafenacin, levothyroxine, levonorgestrel, misoprostol, repaglinide, ambrisentan, amiloride, amlodipine, bepotastine besilate, biperiden, bisoprolol, blonanserin, chlorambucil, dexamethasone, diazepam, enalapril, ergocalciferol, escitalopram oxalate, esomeprazole magnesium hydrate, eszopiclone, ezetimibe, fludarabine, fluticasone furoate, folic acid, haloperidol, isosorbide dinitrate, ivermectin, lenalidomide hydrate, levocetirizine hydrochloride, levonorgestrel, loperamide, loratadine, medroxyprogesterone acetate, methadone, methotrexate, metoclopramide, mitiglinide calcium hydrate, montelukast sodium, norethisterone, paliperidone, phytomenadione or phytonadione, ramelteon, riboflavin, risperidone, rizatriptan benzoate, ropinirole hydrochloride, rosuvastatin calcium, senna extract, silodosin, solifenacin succinate and warfarin.

These active ingredients and medicinal ingredients may be blended into the composition of the present embodiment together with the cellulose composition of the present embodiment in a finely pulverized state. For example, the active ingredient used in the present specification may be finely pulverized to particles having an average particle size of 1 μm or more and 40 μm or less for the purpose of improving the dispersibility of the active ingredient or improving the mixing uniformity of the active ingredient having medicinal effects in a trace amount. The average particle size of the active ingredient is more preferably 1 μm or more and 20 μm or less, and still more preferably 1 μm or more and 10 μm or less.

[Other Additives]

The composition of the present embodiment may further contain other additives in addition to the above-mentioned active ingredient.

Examples of other additives include excipients, disintegrants, binders, fluidizers, lubricants and flavoring agents.

Examples of the excipient include those classified as excipients in "Japanese Pharmaceutical Excipients Directory 2016" (published by Yakuji Nippo, Ltd.), such as acrylated starch, L-asparagic acid, aminoethyl sulfonic acid, aminoacetate, wheat gluten (powder), gum arabic, powdered acacia, alginic acid, sodium alginate, pregelatinized starch, light gravel granule, inositol, ethyl cellulose, ethylene-vinyl acetate copolymer, sodium chloride, olive oil, kaolin, cacao butter, casein, fructose, light gravel granule, carmellose, carmellose sodium, hydrous silicon dioxide, dry yeast, dried aluminum hydroxide gel, dried sodium sulfate, dried magnesium sulfate, agar, agar powder, xylitol, citric acid, sodium citrate, disodium citrate, glycerin, calcium glycerophosphate, sodium gluconate, L-glutamine, clay, clay 3, clay grain, croscannellose sodium, crospovidone, magnesium aluminosilicate, calcium silicate, magnesium silicate, light anhydrous silicic acid, light liquid paraffin, cinnamon powder, crystalline cellulose, crystalline cellulose-carmellose sodium, crystalline cellulose (grain), brown rice malt, synthetic aluminum silicate, synthetic hydrotalcite, sesame oil, wheat flour, wheat starch, wheat germ powder, rice powder, rice starch, potassium acetate, calcium acetate, cellulose acetate phthalate, safflower oil, white beeswax, zinc oxide, titanium oxide, magnesium oxide, β-cyclodextrin, dihydroxyaluminum aminoacetate, 2,6-dibutyl-4-methylphenol, dimethylpolysiloxane, tartaric acid, potassium hydrogen tartrate, plaster, sucrose fatty acid ester, alumina magnesium hydroxide, aluminum hydroxide gel, aluminum hydroxide/sodium hydrogen carbonate coprecipitate, magnesium hydroxide, squalane, stearyl alcohol, stearic acid, calcium stearate, polyoxyl stearate, magnesium stearate, soybean hardened oil, purified gelatine, purified shellac, purified sucrose, purified sucrose spherical granulated powder, cetostearyl alcohol, polyethylene glycol 1000 monocetyl ether, gelatine, sorbitan fatty acid ester, D-sorbitol, tricalcium phosphate, soybean oil, unsaponified soy bean, soy bean lecithin, powdered skim milk, talc, ammonium carbonate, calcium carbonate, magnesium carbonate, neutral anhydrous sodium sulfate, low substitution degree hydroxypropylcellulose, dextran, dextrin, natural aluminum silicate, corn starch, powdered tragacanth, silicon dioxide, calcium lactate, lactose, lactose granulated substance, par filler 101, white shellac, white vaseline, white clay, sucrose, sucrose/starch spherical granulated powder, naked barley green leaf extract, dried powder of bud and leaf juice of naked barley, honey, paraffin, potato starch, semi-digested starch, human serum albumin, hydroxypropyl starch, hydroxypropylcellulose, hydroxypropyl methylcellulose phthalate, phytic acid, glucose, glucose hydrate, partially pregelatinized starch, pullulan, propylene glycol, starch syrup of reduced malt sugar powder, powdered cellulose, pectin, bentonite, sodium polyacrylate, polyoxyethylene alkyl ethers, polyoxyethylene hydrogenated castor oil, polyoxyethylene (105) polyoxypropylene (5) glycol, polyoxyethylene (160) polyoxypropylene (30) glycol, sodium polystyrene sulfonate, polysorbate 80, polyvinylacetal diethylamino acetate, polyvinylpyrrolidone, polyethylene glycol, maltitol, maltose, D-mannitol, water candy, isopropyl myristate, anhydrous lactose, anhydrous calcium hydrogenphosphate, anhydrous calcium phosphate granulated substance, magnesium aluminometasilicate, methyl cellulose, cottonseed powder, cotton oil, haze wax, aluminum monostearate, glyceryl monostearate, sorbitan monostearate, pharmaceutical carbon, peanut oil, aluminum sulfate, calcium sulfate, granular corn starch, liquid paraffin, dl-malic acid, calcium monohydrogen phosphate, calcium hydrogen phosphate, calcium hydrogen phosphate granulated substance, sodium hydrogen phosphate, potassium dihydrogen phosphate, calcium dihydrogen phosphate and sodium dihydrogen phosphate. One of these excipients may be used alone, or two or more types thereof may be used in combination.

Examples of the disintegrant include those classified as disintegrants in "Japanese Pharmaceutical Excipients Directory 2016" (published by Yakuji Nippo, Ltd.), including celluloses such as croscarmellose sodium, carmellose, carmellose calcium, carmellose sodium and low substituted hydroxypropylcellulose; starches such as sodium carboxymethyl starch, hydroxypropyl starch, rice starch, wheat starch, corn starch, potato starch and partially pregelatinized starch; and synthetic polymers such as crospovidone and crospovidone copolymers. One of these disintegrants selected from the above list may be used alone, or two or more types thereof may be used in combination.

Examples of the binder include those classified as binders in "Japanese Pharmaceutical Excipients Directory 2016" (published by Yakuji Nippo, Ltd.), including sugars such as sucrose, glucose, lactose and fructose; sugar alcohols such as mannitol, xylitol, maltitol, erythritol and sorbitol; water-soluble polysaccharides such as gelatine, pullulan, carrageenan, locust bean gum, agar, glucomannan, xanthan gum, tamarind gum, pectin, sodium alginate and gum arabic; celluloses such as crystalline cellulose, powdered cellulose, hydroxypropylcellulose and methyl cellulose; starches such as pregelatinized starch and starch paste; synthetic polymers such as polyvinylpyrrolidone, carboxyvinyl polymers and polyvinyl alcohols; and inorganic compounds such as calcium hydrogen phosphate, calcium carbonate, synthetic hydrotalcite and magnesium aluminosilicate. One of these binders selected from the above list may be used alone, or two or more types thereof may be used in combination.

Examples of the fluidizer include those classified as fluidizers in "Japanese Pharmaceutical Excipients Directory 2016" (published by Yakuji Nippo, Ltd.), including silicon compounds such as hydrous silicon dioxide and light anhydrous silicic acid. One of these fluidizers selected from the above list may be used alone, or two or more types thereof may be used in combination.

Examples of the lubricant include those classified as lubricants in "Japanese Pharmaceutical Excipients Directory 2016" (published by Yakuji Nippo, Ltd.), such as magnesium stearate, calcium stearate, stearic acid, sucrose fatty acid esters and talc. One of these lubricants selected from the above list may be used alone, or two or more types thereof may be used in combination.

Examples of the flavoring agent include those classified as flavoring agents in "Japanese Pharmaceutical Excipients Directory 2016" (published by Yakuji Nippo, Ltd.), such as glutamic acid, fumaric acid, succinic acid, citric acid, sodium citrate, tartaric acid, malic acid, ascorbic acid, sodium chloride and l-menthol. One of these flavoring agents selected from the above list may be used alone, or two or more types thereof may be used in combination.

Examples of the fragrance include those classified as fragrances or flavors in "Japanese Pharmaceutical Excipients Directory 2016" (published by Yakuji Nippo, Ltd.), including orange, vanilla, strawberry, yogurt, menthol, oils such as fennel oil, cinnamon oil, orange peel oil and peppermint oil; and green tea powder. One of these fragrances or flavors selected from the above list may be used alone, or two or more types thereof may be used in combination.

Examples of the coloring agent include those classified as coloring agents in "Japanese Pharmaceutical Excipients Directory 2016" (published by Yakuji Nippo, Ltd.), including food dyes such as food red No. 3, food yellow No. 5 and food blue No. 1; sodium copper chlorophyllin, titanium oxide and riboflavin. One of these coloring agents selected from the above list may be used alone, or two or more types thereof may be used in combination.

Examples of the sweetener include those classified as sweeteners in "Japanese Pharmaceutical Excipients Directory 2016" (published by Yakuji Nippo, Ltd.), such as aspartame, saccharin, dipotassium glycyrrhizinate, stevia, maltose, maltitol, starch syrup and powdered sweet hydrangea leaf. One of these sweeteners selected from the above list may be used alone, or two or more types thereof may be used in combination.

<Method for Producing Tablet>

Hereinafter, a method for producing a tablet by tableting a composition containing one or more active ingredients and the cellulose composition of the present embodiment (method for producing a tablet of the present embodiment) will be described, but this is merely an example, and the effects of the present embodiment are not limited to the following method.

As a method for producing a tablet, a method can be employed in which the active ingredient and the cellulose composition of the present embodiment are mixed and then compression molded. At this time, in addition to the active ingredient, other additives may be added, if necessary. Examples of other additives include at least one component selected from the above-mentioned excipients, disintegrants, binders, fluidizers, lubricants, flavoring agents, fragrances, coloring agents, sweeteners, solubilizing agents and the like.

The order of addition of each component is not particularly limited, and either i) a method of collectively mixing the active ingredient, the cellulose composition of the present embodiment, and, if necessary, other additives, followed by compression molding; or ii) a method in which the active ingredient and at least one additive selected from a fluidizer and a lubricant are pretreated and mixed, and then the cellulose composition of the present embodiment, and if necessary, other additives are mixed, followed by compression molding, may be used. From the viewpoint of ease of operation, the method i) is preferable. It is also possible to add a lubricant to a mixture powder for compression molding obtained in the method i) or ii), which is further mixed and then subjected to compression molding. The method for adding each component is not particularly limited as long as it is a commonly used method, and they may be continuously added or collectively charged using a small suction transport apparatus, an air transport apparatus, a bucket conveyor, a pneumatic transport apparatus, a vacuum conveyer, a vibration type quantitative metering feeder, a sprayer, a funnel and the like. As the spraying method, either a method of spraying an active ingredient solution/dispersion liquid using a pressure nozzle, a two fluid nozzle, a four fluid nozzle, a rotating disk, an ultrasonic nozzle or the like, or a method of dropwise adding an active ingredient solution/dispersion liquid from a tubular nozzle may be used.

The mixing method is not particularly limited as long as it is a commonly used method, and a container rotating mixer such as a V-type, W-type, double cone type or container tack type mixer; a stirring mixer such as a high-speed stirring type, universal stirring type, ribbon type, pug type or Nauta mixer; a high-speed fluid type mixer, a drum type mixer or a fluidized bed type mixer may be used. Further, it is also possible to use a container shaking type mixer such as a shaker.

The compression molding method of the composition is not particularly limited as long as it is a commonly used method, and may be a method of compression molding into a desired shape using a mortar and a pestle, or a method of cutting into a desired shape after compression molding into a sheet shape in advance. As a compression molding machine, for example, a compressor such as a hydrostatic press, a roller type press such as a briquetting roller type press or a smoothing roller type press, a single punch tableting machine, or a rotary tableting machine can be used.

The method for dissolving or dispersing the active ingredient in a medium is not particularly limited as long as it is a commonly used dissolution or dispersion method, and a stirring and mixing method using a stirring blade such as a one-direction rotation type, multi-axis rotation type, reciprocal inversion type, vertical movement type, rotation+vertical movement type, and piping type such as a portable mixer, a three-dimensional mixer, and a side-wall mixer; a jet type stirring and mixing method such as a line mixer; a gas-blowing stirring and mixing method; a mixing method using a high-shear homogenizer, a high-pressure homogenizer, an ultrasonic homogenizer or the like; a container shaking type mixing method using a shaker or the like may be used.

The solvent used in the above-mentioned production method is not particularly limited as long as it is used for pharmaceutical products, but for example, at least any one of water and an organic solvent may be used. Examples of the organic solvent include those classified as solvents in "Japanese Pharmaceutical Excipients Directory 2016" (published by Yakuji Nippo, Ltd.), including alcohols such as methanol, ethanol, isopropyl alcohol, butyl alcohol, 2-methylbutyl alcohol and benzyl alcohol; hydrocarbons such as pentane, hexane, heptane and cyclohexane; and ketones such as acetone and ethyl methyl ketone. One of these solvents may be used alone, two or more types thereof may be used in combination, or the solid content may be dispersed once in one medium and then dispersed in a different medium after removing the initial medium.

When dissolving the active ingredient in a medium, a water-soluble polymer, oil and fat, a surfactant or the like may be used as a solubilizing agent. As the water-soluble polymer, oil and fat, and surfactant used as a solubilizing agent, those described in "Japanese Pharmaceutical Excipients Directory 2016" (published by Yakuji Nippo, Ltd.) can be suitably used. One of these may be used alone, or two or more types thereof may be used in combination.

A molded product in the present specification has a form of granules, fine granules, slugs, tablets and the like, and contains the cellulose composition of the present embodiment, one or more active ingredients and, if necessary, other additives.

Examples of the method for molding into a tablet include a direct tableting method which involves directly compressing and molding a mixture of the active ingredient and the cellulose composition of the present embodiment, or a mixture of one or more active ingredients and the cellulose composition of the present embodiment, and if necessary, other additives. Other production methods for a multicore tablet having as an inner core a tablet which is preliminarily compressed and molded, or a multilayer tablet in which a plurality of molded products prepared by preliminary compression are stacked and compressed again may be used. The direct tableting method is preferable from the viewpoint of productivity and ease of process control.

The compression molded tablet (molded product) may be further coated. Examples of the coating agent used in this case include coating agents described in "Japanese Pharmaceutical Excipients Directory 2016" (published by Yakuji Nippo, Ltd.). One of these coating agents may be used alone, or two or more types thereof may be used in combination.

The granulation method used in the production process through a granulation step includes dry granulation, wet granulation, heating granulation, spray granulation, and microencapsulation. More specifically, fluidized bed granulation, stirring granulation, extrusion granulation, crushing granulation and tumbling granulation methods are effective as the wet granulation method, and in the fluidized bed granulation method, a binding liquid is sprayed on a fluidized powder for granulation in a fluidized bed granulator. In the stirring granulation method, the powder is mixed, kneaded, and granulated at the same time in a sealed structure by rotating a stirring blade in a mixing vessel while adding a binding liquid. In the extrusion granulation method, a wet mass kneaded by the addition of a binding liquid is forcibly extruded from a screen of a suitable size by a screw type or basket type method for granulation. In the crushing granulation method, a wet mass kneaded by the addition of a binding liquid is sheared and crushed by the rotary blade of a granulator, and ejected from the circumferential screen by the centrifugal force for granulation. In the tumbling granulation method, the powder is rolled by the centrifugal force of a rotating rotor, and at this time, spherical granules having a uniform particle size are grown at an accelerating rate for granulation by a binding liquid sprayed from a spray gun.

As the method for drying the granulated product, any of a hot air heating type method (shelf drying, vacuum drying, and fluidized bed drying), a conductive heat transfer type (pan type, shelf box type, and drum type) method and freeze drying can also be used. In the hot air heating type method, hot air is brought into direct contact with the additive, and at the same time, the evaporated water is removed. In the conductive heat transfer type method, the additive is indirectly heated through a heat transfer wall. In the freeze drying method, the additive is frozen at −10° C. or higher and 40° C. or lower, and then heated under high vacuum ($1.3\times10^{-5}$ MPa or higher and $2.6\times10^{-4}$ MPa or lower) to sublimate and remove water.

EXAMPLES

The present embodiment will be described below in detail with reference to Examples and Comparative Examples, but the present embodiment is not limited thereto. The physical properties and their measuring methods in Examples and Comparative Examples are as follows. It should be noted that when a sample contained a large amount of water, various physical properties were measured by pre-drying the sample to a water content of about 3.5% by mass or more and 4.5% by mass or less.

<Method for Analyzing Composition of Cellulose Composition>

[Analysis 1]

(Method for Measuring the Content of Water-Soluble Substance in the Cellulose Composition)

The content of a water-soluble substance in a cellulose composition was measured by the following procedure with reference to the method of the purity test (2) for crystalline cellulose as defined in the 17th revised Japanese Pharmacopoeia.

80 mL of purified water was added to 5.0 g of the cellulose composition, and the resulting mixture was shaken and mixed for 10 minutes. Then, a solution containing the cellulose composition was subjected to suction filtration using a filter paper for quantitative analysis (No. 5C). The filtrate was evaporated to dryness in a beaker of known mass so as not to be charred, and then dried at 105° C. for 1 hour and allowed to cool in a desiccator to obtain a residue. Then, the mass of the obtained residue was weighed to determine the mass of the residue. Each powder was measured twice and the average value was adopted. Further, a test performed only with 80 mL of purified water without adding 5.0 g of the cellulose composition in the above operation was defined as a blank test, and the amount of the water-soluble substance detected in the blank test was subtracted from the measured value to obtain a value. This value was rounded off to the first decimal place and was taken as the measured value of the amount of water-soluble substance. The amount of water-soluble substance obtained by this test method is the amount of water-soluble substance contained in 5 g of the cellulose composition.

[Analysis 2]
(Measurement of Contents of Sugars (Glucose, Sorbitol and Cellobiose) in Cellulose Composition)

The entire amount of a dried product of the water-soluble substance obtained in the above section entitled "Analysis 1" was redissolved by adding 10 mL of a 50% (v/v) acetonitrile aqueous solution, followed by filtration with a filter (0.20 μm), and the contents of glucose, sorbitol and cellobiose were measured by LC/MS. The measurement conditions for LC/MS measurements are as follows.

A precision balance was used when preparing or diluting measurement solutions, and the sample concentration and dilution rate were determined using the weight.

In addition, in measuring the contents of glucose, sorbitol and cellobiose, solutions of glucose, sorbitol and cellobiose with known concentrations that were prepared using commercially available products were analyzed by LC/MS, the retention time and the peak area of m/z ion chromatograms corresponding to each sugar were obtained, and calibration curves (sample concentration—peak area) were created. Using this calibration curve, the content of each sugar in the water-soluble substance (5 g of the cellulose composition) was determined. It should be noted that the content of each sugar is indicated by a value obtained by rounding off the second decimal place.

(Measurement Conditions)

LC system: Nexera, manufactured by Shimadzu Corporation

Column Shodex Asahipak NH2P-50 2D (2 mm I.D.×150 mm), manufactured by Showa Denko K.K.

Column temperature: 40° C.

Detector: PDA detector, 200 to 400 nm

Flow rate: 0.3 mL/min

Mobile phase: A=purified water, B=acetonitrile

Gradient: gradient conditions are shown in Table 1 below.

Injection volume: 10 μL

MS system: Synapt G2, manufactured by Waters Corporation

Ionization condition: ESI$^-$

Scan range: m/z 50 to 2,000

TABLE 1

| Time (min) | A (%) | B (%) |
| --- | --- | --- |
| 0 | 10 | 90 |
| 15 | 50 | 50 |
| 15.1 | 10 | 90 |
| 25 | 10 | 90 |

For reference, the detected ions (m/z) and retention time of each component observed under the above measurement conditions are shown in Table 2 below.

TABLE 2

| | Detected ions (m/z) | Retention time (min) |
| --- | --- | --- |
| Sorbitol | 181.07 [M − H]$^-$ | 5.9 |
| Glucose | 179.06 [M − H]$^-$ | 6.1 |
| Cellobiose | 341.11 [M − H]$^-$ | 7.8 |

<Method for Measuring Powder Physical Properties>

[Physical Property 1]
(Water Absorption Rate)

The water absorption rate was measured using a Peneto Analyzer (model: PNT-N, manufactured by Hosokawa Micron Corporation).

More specifically, first, in order to suppress variations in the measured value due to static electricity, before the measurement, the bottom surface of a measurement cell was wiped with a wrung towel soaked with an aqueous solution containing 1% of household detergent, and was naturally dried. A bottom plate and filter paper were set in the measurement cell, 5 g of the cellulose composition was placed therein, and tapping was performed with an attached tapping device (300 times, 18 mm, weight: 198 g). The tapped sample was attached to a cell holder and attached to the main body of the Peneto Analyzer. The measurement was carried out at room temperature (25° C.) with a solvent (purified water, 300 mL) under the following elevating conditions at the time of measurement ((1) 1.5 mm/s, (2) 0.1 mm/s, (3) 0.5 mm/s, manual operation: 1.5 mm/s). A water absorption curve obtained by plotting the square of mass (g$^2$) on the vertical axis and the measurement time (elapsed time from the start of water absorption) (s) on the horizontal axis was linearly approximated in a linear region of the water absorption curve (region from ⅓ to ⅔ of the saturation of water absorption), and the slope of an approximate straight line was obtained as a permeation rate coefficient (g$^2$/s).

[Physical Property 2]
(Average Particle Size)

The measurement was carried out using a laser diffraction type particle size distribution meter (LA-950 V2 (product name), manufactured by Horiba, Ltd.) in a dry measurement mode with a compressed air pressure of 0.10 MPa, a feeder speed of 160, a feeder initial rate coefficient of 1.2 and a refractive index of 1.51. The particle size at a cumulative volume of 50% obtained by the measurement was taken as the average particle size (μm) of the cellulose composition.

[Physical Property 3]
(Loose Bulk Density)

For the measurement, a cellulose composition having a water content adjusted to 3.5% by mass or more and 4.5% by mass or less was used. When the range of the water content of the cellulose composition was out of the lower range, the water content was adjusted by allowing the cellulose powder to absorb water in a constant temperature and humidity chamber or the like. Further, when the range of the water content of the cellulose composition was out of the upper range, hot air at 60° C. was evenly applied to the cellulose composition in a hot air oven to adjust the water content within the range.

A Scott volumeter (model: ASTM B-329-85, manufactured by Tsutsui Scientific Instruments Co., Ltd.) was used for the measurement of the loose bulk density of the cellulose composition, and the cellulose composition was filled into a 25 mL cylindrical metal container through a sieve (opening: 1 mm). The cellulose composition contained in the 25 mL cylindrical metal container was leveled, and the mass (g) of the cellulose composition in the container was divided by a volume of 25 mL to determine the loose bulk density (g/mL). The measurement was carried out 5 times and the average value was determined.

[Physical Property 4]
(Packed Bulk Density)

For the measurement, a cellulose composition having a water content adjusted to 3.5% by mass or more and 4.5% by mass or less was used. The water content of the cellulose composition was adjusted so as to be within the range by using the method described in the section entitled "Physical property 3". The packed bulk density (packed apparent specific gravity) (g/mL) was calculated with a powder physical property measuring machine (PT-R, manufactured by Hosokawa Micron Corporation). The sieve used had an opening of 710 μm, and a funnel made of a metal (coated with antistatic spray) and having an inner diameter of 0.8 cm was used. The "VIBRATION" operation was carried out at 2.0 (power supply: AC100V, 60 Hz).

[Physical Property 5]
(Compression Rate)

The compression rate of each cellulose composition was calculated by a formula shown below.

Compression rate(%)=([packed bulk density]−[loose bulk density])/[packed bulk density]×100

[Physical Property 6]
(Ratio of Major Axis with Respect to Minor Axis of Cellulose Particles (L/D))

The cellulose composition was dispersed on a glass plate and photographed using a microscope (VHX-1,000, manufactured by Keyence Corporation) at a magnification of 500 times. The captured image was analyzed by the following procedure using image processing analysis system software (Image Hyper II, manufactured by DigiMo Co., Ltd.), and the aspect ratio (ratio of major axis with respect to minor axis; L/D) of the particles was measured. The measurements were carried out on at least 50 particles and the average value was determined.

(1) Step 1: Binarization Process

An image taken with the microscope was captured in the analysis software in monochrome, and the scale of the image was set by a two-point distance method. Next, the "Otsu method" was selected in the binarization process, and the threshold value was set. Since the optimum threshold value differs for each image, the threshold value was selected so as to coincide with the shape of the original particle as much as possible while comparing with the original image.

(2) Step 2: Manual Binarization Correction

While comparing with the original image taken, particles that did not give appropriate measurement results, such as particles that overlapped with each other, particles that protruded from the screen, and particles that were unclear and had blurred outlines were deleted and excluded from the measurement object.

(3) Step 3: Hole Filling

In the "hole filling" mode, "8" was selected for "neighborhood" and the "hole filling" operation was executed. Next, the image was compared with the original image again by "manual binary image correction", and it was confirmed whether the correction was performed normally. If the correction was not performed normally, the manual correction was performed again.

(4) Step 4: Image Measurement

After setting the number of deleted pixels to "100" and selecting "8" for "neighborhood", the "image measurement" operation was executed. The measurement results of "major axis" and "minor axis" for each particle to be measured were displayed on a personal computer. A value obtained by dividing the "major axis" by the "minor axis" was used as the aspect ratio.

<Tablet Evaluation Method>

Orally disintegrating tablets (OD tablets) and tablets were produced and evaluated in various ways using the methods shown below.

[Production of OD Tablets]

A formulated powder shown below was placed in a plastic bag and shaken for 1 minute to mix. Then, the mixed powder was sieved through a 710 μm sieve, and a lubricant (sodium stearyl fumarate) was further added so as to be 1% by mass with respect to the total mass of the OD tablet, followed by mixing for 30 seconds. Subsequently, the mixed powder was tableted with a rotary tablet press (Clean Press Correct 12HUK, manufactured by Kikusui Seisakusho Ltd., 12 punches, turntable: 54 rpm) to obtain 200 mg of a φ8 mm-12R tablet. The tableting pressure was appropriately set so that the tablet hardness was 80 N or more and 90 N or less.

(Formulation)

Mannitol for direct compression (Mannogem EZ, manufactured by Asahi Kasei Corporation): 70% by mass Partially pregelatinized starch (PCS, PC-10, manufactured by Asahi Kasei Corporation): 10% by mass Croscarmellose sodium (Kiccolate ND-200, manufactured by Asahi Kasei Corporation): 5% by mass Cellulose composition: 15% by mass It should be noted that the content of each component in the above formulation is a ratio with respect to the total mass of the above components.

[Evaluation 1]
(Hardness)

The hardness of each OD tablet was measured with a hardness tester (DR. SCHLEUNIGER Tablet Tester 8M) after 20 hours or more and 48 hours or less had elapsed immediately after tableting. The average value of 5 tablets at each tableting pressure was taken as the hardness (N) of the OD tablet.

[Evaluation 2]
(Disintegration Rime in Oral Cavity)

An orally disintegrating tablet tester (model: ODT-101, manufactured by Toyama Sangyo Co., Ltd.) was used for the measurement of the disintegration time in oral cavity. The disintegration time was measured by placing and setting the OD tablet on the left end of a hole in the center of a sample fixing frame under the conditions of test liquid: water (37±1° C.), weight diameter: φ20 mm, weight mass: 20 g, rotational speed: 140 rpm, OD tablet thickness: 4.0 mm. The average value of 6 tablets was taken as the disintegration time of OD tablet in oral cavity.

[Evaluation 3]
(Core Residue)

The core residue of the OD tablet was evaluated using an orally disintegrating tablet tester. First, the disintegration time in oral cavity described in the section entitled "Evaluation 2" was measured to determine the disintegration time in oral cavity. Next, in order to evaluate the core residue of the OD tablet, the orally disintegrating tablet tester was stopped at "75% of the obtained disintegration time in oral cavity" from the start of counting of the disintegration time of the OD tablet, and it was confirmed whether there was any solid fragment of the OD tablet left. The core residue was evaluated in accordance with the following evaluation criteria. The test was performed three times, and those scored as (+) more than once were evaluated as (+).

(Evaluation Criteria)

(+) those with remaining solid fragments of OD tablet (−) those with no remaining solid fragments of OD tablet

[Production of Tablets for Storage Stability Test]

A powder obtained by mixing the cellulose composition and aminophylline (cellulose composition: aminophylline=1:1 (part by mass)) in a plastic bag was tableted with a static pressure tableting machine (tableting pressure: 7 kN, retention time: 10 seconds) to obtain 500 mg flat tablets (φ11.3 mm).

[Evaluation 4]
(Storage Stability)

The reactivity between the cellulose composition and the drug was confirmed by the change in whiteness of the tablet immediately after tableting and after storage.

The tablets obtained by the above production method were used immediately after tableting to determine the values of brightness (L), saturation (a) (green to red) and saturation (b) (blue to yellow) by using a spectroscopic colorimeter (SE-2000, manufactured by Nippon Denshoku Industries Co., Ltd.). Subsequently, the whiteness was calculated using the following formula.

Whiteness=$100-[(100-L)^2+a^2+b^2]^{0.5}$

In addition, the obtained tablets were placed in a glass bottle, sealed, and stored for 1 month in a constant temperature and humidity chamber set at a temperature of 40° C. and a humidity of 75% RH, and the values of (L), (a) and (b) after storage were also measured with a spectroscopic colorimeter, and the whiteness after the storage stability test was calculated using the above formula.

The change in whiteness of the tablet immediately after tableting (before storage) and after the storage stability test (after storage) was calculated using the following formula.

Change in whiteness=whiteness(before storage)−whiteness(after storage)

It should be noted that when the absolute value of the change in whiteness exceeds 10%, since the degree of color change can be visually recognized, those having the absolute value of the change in whiteness of 10% or less were evaluated as having a favorable level of storage stability.

<Preparation of Wet Floc>

Preparation Example 1

(Preparation of Wet Floc X)

2 kg of shredded commercially available pulp and 30 L of an aqueous hydrochloric acid solution were placed in a low-speed stirrer (30 LGL reactor (product name) manufactured by Ikebukuro Horo Kogyo Co., Ltd.), and the resulting mixture was hydrolyzed while stirring (reaction conditions: hydrochloric acid concentration: 0.5%, reaction temperature: 120° C., reaction time: 1.0 hour, stirring speed: 220 rpm) to obtain an acid insoluble residue. The obtained acid insoluble residue was thoroughly washed with pure water until the electrical conductivity of the filtrate became less than 100 μS/cm, and then subjected to filtration to obtain wet floc X. When the average degree of polymerization of wet floc X was measured by a copper ethylenediamine solution viscosity method described in the identification test (3) for crystalline cellulose in Japanese Pharmacopoeia, the average degree of polymerization was 170.

<Production of Cellulose Composition>

Example 1

(Production of Cellulose Composition A)

The wet floc X was introduced into a 90 L plastic bucket, pure water was added thereto so that the total solid content concentration was 10% by mass, and the resulting mixture was dispersed by a three-one motor to prepare 30 kg of a dispersion liquid. The dispersion liquid was neutralized with aqueous ammonia while stirring (pH was 7.5 or more and 8.0 or less after neutralization), and after adding 1.56 g of glucose, the resulting mixture was stirred and spray dried (conditions: dispersion liquid supply rate: 6 kg/hr; inlet temperature: 180° C. or higher and 220° C. or lower; outlet temperature: 50° C. or higher and 70° C. or lower) to obtain a cellulose composition A. In 5 g of the cellulose composition, the amount of water-soluble substance was 4.9 mg, the amount of glucose was 2.9 mg, the amount of sorbitol was 0.2 mg, and the amount of cellobiose was 0.7 mg.

Example 2

(Production of Cellulose Composition B)

The wet floc X was introduced into a 90 L plastic bucket, pure water was added thereto so that the total solid content concentration was 10% by mass, and the resulting mixture was dispersed by a three-one motor to prepare 30 kg of a dispersion liquid. The dispersion liquid was neutralized with aqueous ammonia while stirring (pH was 7.5 or more and 8.0 or less after neutralization), and after adding 0.81 g of glucose, the resulting mixture was stirred and spray dried (conditions: dispersion liquid supply rate: 6 kg/hr; inlet temperature: 180° C. or higher and 220° C. or lower; outlet temperature: 50° C. or higher and 70° C. or lower) to obtain a cellulose composition B. In 5 g of the cellulose composition, the amount of water-soluble substance was 3.7 mg, the amount of glucose was 1.7 mg, the amount of sorbitol was 0.2 mg, and the amount of cellobiose was 0.7 mg.

Example 3

(Production of Cellulose Composition C)

800 g of the cellulose composition B obtained in Example 2 was charged into a high-speed stirring granulator and granulated, dried in a fluidized bed, and then sieved through a 500 μm sieve to obtain a cellulose composition C (granulation conditions: amount of water added: 600 g; granulation time: 20 minutes; main blade: 400 rpm, cross screw: 500 rpm; drying condition: drying temperature 80° C.). In 5 g of the cellulose composition, the amount of water-soluble substance was 3.4 mg, the amount of glucose was 1.6 mg, the amount of sorbitol was 0.2 mg, and the amount of cellobiose was 0.6 mg.

Example 4

(Production of Cellulose Composition D)

The cellulose composition B obtained in Example 2 was pulverized with a jet mill pulverizer to obtain a cellulose composition D. In 5 g of the cellulose composition, the amount of water-soluble substance was 4.0 mg, the amount of glucose was 1.8 mg, the amount of sorbitol was 0.2 mg, and the amount of cellobiose was 0.8 mg.

Example 5

(Production of Cellulose Composition E)

The cellulose composition B obtained in Example 2 was pulverized with an ultracentrifugal pulverizer to obtain a cellulose composition E. In 5 g of the cellulose composition, the amount of water-soluble substance was 4.3 mg, the amount of glucose was 2.0 mg, the amount of sorbitol was 0.2 mg, and the amount of cellobiose was 0.8 mg.

Example 6

(Production of Cellulose Composition F)

The wet floc X was introduced into a 90 L plastic bucket, pure water was added thereto so that the total solid content concentration was 10% by mass, and the resulting mixture was dispersed by a three-one motor to prepare 30 kg of a dispersion liquid. The dispersion liquid was neutralized with aqueous ammonia while stirring (pH was 7.5 or more and 8.0 or less after neutralization), and after adding 0.19 g of glucose, the resulting mixture was stirred and spray dried (conditions: dispersion liquid supply rate: 6 kg/hr; inlet temperature: 180° C. or higher and 220° C. or lower; outlet temperature: 50° C. or higher and 70° C. or lower) to obtain a cellulose composition F. In 5 g of the cellulose composition, the amount of water-soluble substance was 2.7 mg, the amount of glucose was 0.7 mg, the amount of sorbitol was 0.2 mg, and the amount of cellobiose was 0.7 mg.

Example 7

(Production of Cellulose Composition G)

The wet floc X was introduced into a 90 L plastic bucket, pure water was added thereto so that the total solid content concentration was 10% by mass, and the resulting mixture was dispersed by a three-one motor to prepare 30 kg of a dispersion liquid. The dispersion liquid was neutralized with aqueous ammonia while stirring (pH was 7.5 or more and 8.0 or less after neutralization), and after adding 2.0 g of sorbitol, the resulting mixture was stirred and spray dried (conditions: dispersion liquid supply rate: 6 kg/hr; inlet temperature: 180° C. or higher and 220° C. or lower; outlet temperature: 50° C. or higher and 70° C. or lower) to obtain a cellulose composition G. In 5 g of the cellulose composition, the amount of water-soluble substance was 5.6 mg, the amount of glucose was 0.4 mg, the amount of sorbitol was 3.4 mg, and the amount of cellobiose was 0.7 mg.

Example 8

(Production of Cellulose Composition H)

The wet floc X was introduced into a 90 L plastic bucket, pure water was added thereto so that the total solid content concentration was 10% by mass, and the resulting mixture was dispersed by a three-one motor to prepare 30 kg of a dispersion liquid. The dispersion liquid was neutralized with aqueous ammonia while stirring (pH was 7.5 or more and 8.0 or less after neutralization), and after adding 1.0 g of sorbitol, the resulting mixture was stirred and spray dried (conditions: dispersion liquid supply rate: 6 kg/hr; inlet temperature: 180° C. or higher and 220° C. or lower; outlet temperature: 50° C. or higher and 70° C. or lower) to obtain a cellulose composition H. In 5 g of the cellulose composition, the amount of water-soluble substance was 4.0 mg, the amount of glucose was 0.4 mg, the amount of sorbitol was 1.8 mg, and the amount of cellobiose was 0.7 mg.

Example 9

(Production of Cellulose Composition I)

800 g of the cellulose composition H obtained in Example 8 was charged into a high-speed stirring granulator and granulated, dried in a fluidized bed, and then sieved through a 500 μm sieve to obtain a cellulose composition I. The granulation conditions and drying conditions were the same as those in Example 3. In 5 g of the cellulose composition, the amount of water-soluble substance was 3.8 mg, the amount of glucose was 0.4 mg, the amount of sorbitol was 1.7 mg, and the amount of cellobiose was 0.7 mg.

Example 10

(Production of Cellulose Composition J)

The cellulose composition H obtained in Example 8 was pulverized with a jet mill pulverizer to obtain a cellulose composition J. In 5 g of the cellulose composition, the amount of water-soluble substance was 4.2 mg, the amount of glucose was 0.4 mg, the amount of sorbitol was 1.9 mg, and the amount of cellobiose was 0.7 mg.

Example 11

(Production of Cellulose Composition K)

The cellulose composition H obtained in Example 8 was pulverized with an ultracentrifugal pulverizer to obtain a cellulose composition K. In 5 g of the cellulose composition, the amount of water-soluble substance was 4.5 mg, the amount of glucose was 0.5 mg, the amount of sorbitol was 2.0 mg, and the amount of cellobiose was 0.8 mg.

Example 12

(Production of Cellulose Composition L)

The wet floc X was introduced into a 90 L plastic bucket, pure water was added thereto so that the total solid content concentration was 10% by mass, and the resulting mixture was dispersed by a three-one motor to prepare 30 kg of a dispersion liquid. The dispersion liquid was neutralized with aqueous ammonia while stirring (pH was 7.5 or more and 8.0 or less after neutralization), and after adding 0.13 g of sorbitol, the resulting mixture was stirred and spray dried (conditions: dispersion liquid supply rate: 6 kg/hr; inlet temperature: 180° C. or higher and 220° C. or lower; outlet temperature: 50° C. or higher and 70° C. or lower) to obtain a cellulose composition L. In 5 g of the cellulose composition, the amount of water-soluble substance was 2.6 mg, the amount of glucose was 0.4 mg, the amount of sorbitol was 0.4 mg, and the amount of cellobiose was 0.7 mg.

Comparative Example 1

(Production of Cellulose Composition M)

The wet floc X was introduced into a 90 L plastic bucket, pure water was added thereto so that the total solid content concentration was 10% by mass, and the resulting mixture was dispersed by a three-one motor to prepare 30 kg of a dispersion liquid. The dispersion liquid was neutralized with aqueous ammonia while stirring (pH was 7.5 or more and 8.0 or less after neutralization), and the resulting mixture was stirred and spray dried without adding glucose (conditions: dispersion liquid supply rate: 6 kg/hr; inlet temperature: 180° C. or higher and 220° C. or lower; outlet temperature: 50° C. or higher and 70° C. or lower) to obtain a cellulose composition M. In 5 g of the cellulose composition, the amount of water-soluble substance was 2.4 mg, the amount of glucose was 0.4 mg, the amount of sorbitol was 0.2 mg, and the amount of cellobiose was 0.7 mg.

Comparative Example 2

(Production of Cellulose Composition N)

The wet floc X was introduced into a 90 L plastic bucket, pure water was added thereto so that the total solid content concentration was 10% by mass, and the resulting mixture was dispersed by a three-one motor to prepare 30 kg of a dispersion liquid. The dispersion liquid was neutralized with aqueous ammonia while stirring (pH was 7.5 or more and 8.0 or less after neutralization), and after adding 2.31 g of glucose, the resulting mixture was stirred and spray dried (conditions: dispersion liquid supply rate: 6 kg/hr; inlet temperature: 180° C. or higher and 220° C. or lower; outlet temperature: 50° C. or higher and 70° C. or lower) to obtain a cellulose composition N. In 5 g of the cellulose composition, the amount of water-soluble substance was 6.1 mg, the amount of glucose was 4.1 mg, the amount of sorbitol was 0.2 mg, and the amount of cellobiose was 0.7 mg.

Comparative Example 3

(Production of Cellulose Mixture O)

50 mg of powdered glucose was added to 100 g of the cellulose composition M obtained in Comparative Example 1, and the resulting mixture was shaken and mixed using a plastic bag to obtain a cellulose mixture O as a physical mixture corresponding to the composition of the cellulose composition A.

For each cellulose composition obtained in Examples and Comparative Examples, various physical properties were measured by using the methods described above, and after producing OD tablets and tablets, each evaluation was performed. The results are shown in Tables 3 to 6.

TABLE 3

| | | | Ex. 1 | Ex. 2 | Ex. 3 | Ex. 4 | Ex. 5 | Ex. 6 |
|---|---|---|---|---|---|---|---|---|
| | Cellulose composition | | A | B | C | D | E | F |
| Production conditions | Wet floc | | X | X | X | X | X | X |
| | Solid content of floc dispersion | [mass %] | 10 | 10 | 10 | 10 | 10 | 10 |
| | Amount of glucose added | [g] | 1.56 | 0.81 | 0.81 | 0.81 | 0.81 | 0.19 |
| | Amount of sorbitol added | [g] | 0 | 0 | 0 | 0 | 0 | 0 |
| Composition | Content of water-soluble substance in 5 g of cellulose composition | [mg] | 4.9 | 3.7 | 3.4 | 4.0 | 4.3 | 2.7 |
| | Content of glucose in 5 g of cellulose composition | [mg] | 2.9 | 1.7 | 1.6 | 1.8 | 2.0 | 0.7 |
| | Content of sorbitol in 5 g of cellulose composition | [mg] | 0.2 | 0.2 | 0.2 | 0.2 | 0.2 | 0.2 |
| | Content of cellobiose in 5 g of cellulose composition | [mg] | 0.7 | 0.7 | 0.6 | 0.8 | 0.8 | 0.7 |
| | Contents of monosaccharides (glucose, sorbitol) in 5 g of cellulose composition | [mg] | 3.1 | 1.9 | 1.7 | 2.1 | 2.2 | 0.9 |
| Physical properties | Water absorption rate | [g$^2$/s] | 5.1 | 4.1 | 3.3 | 6.2 | 3.4 | 2.6 |
| | Average particle size | [μm] | 59 | 55 | 131 | 33 | 18 | 52 |
| | Loose bulk density | [g/mL] | 0.29 | 0.26 | 0.33 | 0.19 | 0.14 | 0.24 |
| | Packed bulk density | [g/mL] | 0.46 | 0.42 | 0.43 | 0.34 | 0.33 | 0.42 |
| | Compression rate | [—] | 37 | 38 | 24 | 44 | 58 | 43 |
| | L/D | [—] | 2.3 | 2.4 | 1.8 | 3.2 | 2.4 | 2.3 |
| Evaluation | Tableting pressure during production of orally disintegrating tablet | [kN] | 8.0 | 7.5 | 8.0 | 7.0 | 6.5 | 7.5 |
| | Disintegration time in oral cavity | [s] | 23 | 25 | 27 | 23 | 25 | 29 |
| | Core residue | [—] | (—) | (—) | (—) | (—) | (—) | (—) |
| | Storage stability (change in whiteness) | [%] | −9 | −7 | −6 | −7 | −8 | −4 |

TABLE 4

| | | | Ex. 7 | Ex. 8 | Ex. 9 | Ex. 10 | Ex. 11 | Ex. 12 |
|---|---|---|---|---|---|---|---|---|
| Production conditions | Cellulose composition | | G | H | I | J | K | L |
| | Wet floc | | X | X | X | X | X | X |
| | Solid content of floc dispersion | [mass %] | 10 | 10 | 10 | 10 | 10 | 10 |
| | Amount of glucose added | [g] | 0 | 0 | 0 | 0 | 0 | 0 |
| | Amount of sorbitol added | [g] | 2.00 | 1.00 | 1.00 | 1.00 | 1.00 | 0.13 |
| Composition | Content of water-soluble substance in 5 g of cellulose composition | [mg] | 5.6 | 4.0 | 3.8 | 4.2 | 4.5 | 2.6 |
| | Content of glucose in 5 g of cellulose composition | [mg] | 0.4 | 0.4 | 0.4 | 0.4 | 0.5 | 0.4 |
| | Content of sorbitol in 5 g of cellulose composition | [mg] | 3.4 | 1.8 | 1.7 | 1.9 | 2.0 | 0.4 |
| | Content of cellobiose in 5 g of cellulose composition | [mg] | 0.7 | 0.7 | 0.7 | 0.7 | 0.8 | 0.7 |
| | Contents of monosaccharides (glucose, sorbitol) in 5 g of cellulose composition | [mg] | 3.8 | 2.2 | 2.1 | 2.3 | 2.5 | 0.8 |
| Physical properties | Water absorption rate | [g$^2$/s] | 7.5 | 5.8 | 4.4 | 7.1 | 4.3 | 2.5 |
| | Average particle size | [μm] | 66 | 59 | 133 | 37 | 16 | 54 |
| | Loose bulk density | [g/mL] | 0.30 | 0.27 | 0.34 | 0.21 | 0.16 | 0.24 |
| | Packed bulk density | [g/mL] | 0.47 | 0.44 | 0.44 | 0.37 | 0.37 | 0.41 |
| | Compression rate | [—] | 36 | 38 | 22 | 43 | 57 | 41 |
| | L/D | [—] | 2.4 | 2.3 | 1.7 | 3.3 | 2.6 | 2.4 |
| Evaluation | Tableting pressure during production of orally disintegrating tablet | [kN] | 8.0 | 7.5 | 8.0 | 7.0 | 6.5 | 7.5 |
| | Disintegration time in oral cavity | [s] | 19 | 22 | 26 | 21 | 22 | 28 |
| | Core residue | [—] | (—) | (—) | (—) | (—) | (—) | (—) |
| | Storage stability (change in whiteness) | [%] | −6 | −4 | −3 | −4 | −5 | −3 |

TABLE 5

| | | | Comp. Ex. 1 | Comp. Ex. 2 |
|---|---|---|---|---|
| Production conditions | Cellulose composition | | M | N |
| | Wet floc | | X | X |
| | Solid content of floc dispersion | [mass %] | 10 | 10 |
| | Amount of glucose added | [g] | 0 | 2.31 |
| | Amount of sorbitol added | [g] | 0 | 0 |
| Composition | Content of water-soluble substance in 5 g of cellulose composition | [mg] | 2.4 | 6.1 |
| | Content of glucose in 5 g of cellulose composition | [mg] | 0.4 | 4.1 |
| | Content of sorbitol in 5 g of cellulose composition | [mg] | 0.2 | 0.2 |
| | Content of cellobiose in 5 g of cellulose composition | [mg] | 0.7 | 0.7 |
| | Contents of monosaccharides (glucose, sorbitol) in 5 g of cellulose composition | [mg] | 0.6 | 4.3 |

TABLE 5-continued

|  |  |  | Comp. Ex. 1 | Comp. Ex. 2 |
|---|---|---|---|---|
| Physical properties | Water absorption rate | [$g^2/s$] | 2.3 | 6.2 |
|  | Average particle size | [μm] | 51 | 62 |
|  | Loose bulk density | [g/mL] | 0.24 | 0.30 |
|  | Packed bulk density | [g/mL] | 0.40 | 0.48 |
|  | Compression rate | [—] | 40 | 37 |
|  | L/D | [—] | 2.2 | 2.3 |
| Evaluation | Tableting pressure during production of orally disintegrating tablet | [kN] | 7.5 | 8.0 |
|  | Disintegration time in oral cavity | [s] | 34 | 21 |
|  | Core residue | [—] | (+) | (−) |
|  | Storage stability (change in whiteness) | [%] | −3 | −12 |

TABLE 6

|  |  |  | Comparative Example 3 |
|---|---|---|---|
|  | Cellulose mixture |  | O |
| Evaluation | Tableting pressure during production of orally disintegrating tablet | [kN] | 7.5 |
|  | Disintegration time in oral cavity | [s] | 33 |
|  | Core residue | [—] | (+) |
|  | Storage stability (change in whiteness) | [%] | −8 |

From Tables 3 to 6, it was found that the disintegration properties when formed into OD tablets and storage stability when formed into tablets were favorable when the cellulose compositions A to L (Examples 1 to 12) were used in which the contents of glucose and sorbitol in 5 g of the cellulose composition were 0.7 mg or more and 4.0 mg or less.

In the cellulose compositions A to L (Examples 1 to 12), the disintegration time in oral cavity tended to be shorter as the content of glucose or sorbitol increased.

In addition, the storage stability tended to be further improved, as the content of glucose or sorbitol in 5 g of the cellulose composition decreased.

It should be noted that in the tablet using the cellulose composition A, the change in whiteness was −9%, but the change in color could not be visually confirmed.

On the other hand, in the cellulose composition M (Comparative Example 1) in which the contents of glucose and sorbitol in the cellulose composition was less than 0.7 mg, although the storage stability was favorable, the disintegration time in oral cavity was as long as 34 seconds, and the residual core was observed.

Further, in the cellulose composition N (Comparative Example 2) in which the content of glucose in the cellulose composition was more than 4.0 mg, the disintegration time in oral cavity was 21 seconds, and although there was no core residue, the change in color after storage represented by the change in whiteness of −12% was so large that it could be visually confirmed as compared to the state before storage, and the storage stability was inferior.

Furthermore, in the cellulose mixture O (Comparative Example 3) in which glucose was added to the cellulose composition M so as to be the same amount as that of the cellulose composition A (Example 1), although the storage stability was favorable, the disintegration time in oral cavity was as long as 33 seconds, and the residual core was observed.

INDUSTRIAL APPLICABILITY

According to the cellulose powder of the present embodiment, it is possible to provide a cellulose composition capable of obtaining a tablet having excellent storage stability while maintaining disintegration properties as an orally disintegrating tablet in a favorable manner. The tablet and the orally disintegrating tablet of the present embodiment contain the aforementioned cellulose composition, exhibit favorable disintegration properties as orally disintegrating tablets, and are excellent in storage stability.

The invention claimed is:

1. A cellulose composition comprising cellulose, and a water-soluble substance comprising glucose and sorbitol, wherein a total content of glucose and sorbitol is 0.7 mg or more and 4.0 mg or less per 5 g of said cellulose composition.

2. The cellulose composition according to claim 1, wherein the content of the water-soluble substance is 2.5 mg or more and 12.5 mg or less per 5 g of said cellulose composition.

3. The cellulose composition according to claim 1, wherein a content of glucose is 0.3 mg or more and less than 4.0 mg per 5 g of said cellulose composition.

4. The cellulose composition according to claim 1, wherein a content of sorbitol is 0.2 mg or more and less than 4.0 mg per 5 g of said cellulose composition.

5. The cellulose composition according to claim 1, wherein said cellulose composition is a powder, and an average particle size of the powder is 10 μm or more and 200 μm or less.

6. The cellulose composition according to claim 1, wherein a water absorption rate is 2.0 $g^2/s$ or more and 9.0 $g^2/s$ or less.

7. A tablet comprising the cellulose composition of claim 1.

8. An orally disintegrating tablet comprising the cellulose composition of claim 1.

* * * * *